United States Patent [19]

Hylarides et al.

[11] Patent Number: 4,676,932
[45] Date of Patent: Jun. 30, 1987

[54] SYNTHESIS OF 1-HALOESTRADIOLS

[75] Inventors: Mark D. Hylarides; Fred A. Mettler, Jr., both of Albuquerque, N. Mex.

[73] Assignee: The University of New Mexico, Albuquerque, N. Mex.

[21] Appl. No.: 687,035

[22] Filed: Dec. 28, 1984

Related U.S. Application Data

[63] Continuation-in-part of Ser. No. 597,930, Apr. 9, 1984, Pat. No. 4,584,137.

[51] Int. Cl.$^4$ .................................................. C07J 1/00
[52] U.S. Cl. ................................................... 260/397.5
[58] Field of Search ...................................... 260/397.5

[56] References Cited

U.S. PATENT DOCUMENTS 3,264,330  8/1966  Moersch et al. ................. 260/397.5
4,522,758  6/1985  Ward et al. ....................... 260/397.5

OTHER PUBLICATIONS

Hylarides et al., "Steroids" Nov. 30, 1984, vol. 43, No. 2, pp. 219–224.

*Primary Examiner*—Elbert L. Roberts
*Attorney, Agent, or Firm*—Charles W. Fallow; Martin P. Hoffman; Jean A. Buttmi

[57] ABSTRACT

Estrogens characterized by an aromatic ring of the formula

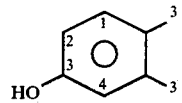

are halogenated by electrophilic substitution of a halo atom at the 1-position of the aromatic ring after protection of the sensitive 3-hydroxyl substituent and amination at the 4-position. Preferred starting materials include estrones or derivatives thereof. The estrones are preferably reduced after masking and amination to form the corresponding estradiols, which are then halogenated, deaminated and deprotected to provide the novel 1-haloestradiols.

3 Claims, No Drawings

SYNTHESIS OF 1-HALOESTRADIOLS

CROSS-REFERENCE TO RELATED APPLICATION

This application is a continuation-in-part of U.S. patent application Ser. No. 597,930, filed Apr. 9, 1984, now U.S. Pat. No. 4,584,137.

BACKGROUND OF THE INVENTION

The use of radiolabelled steroids for in vivo receptor binding assays is well known; generally, the efficacy of particular radiolabelled steriods is evaluated in competitive binding assays employing non-radioactive analogue as competitor. The radiolabelled steroid, to be of use in nuclear medicine applications, should exhibit a high specific activity, good chemical stability, and a high in vivo receptor binding affinity.

Since stability is essential, halogenation of the aromatic ring of native steroids has been proposed, as it is known that steroids in which the aromatic ring of the steroid nucleus is halo-substituted are generally more stable than the same steroids wherein an aliphatic carbon is halo-substituted. In some instances, however, stabilization of steroids by halogenation or radiohalogenation has significantly reduced the biological activity of the steroid so that the derivative is useless as a practical matter in applications requiring a high in vivo binding affinity between the receptor and stabilized compound. For example, estradiol brominated in the 4-position with $^{77}$Br has a high specific activity, and good chemical stability; receptor binding studies, however, indicate that 4-$^{77}$Br-estradiol has a low in vivo binding affinity for estrogen receptors, probably owing to the close proximity of the halo and hydroxyl substituents on the 3-phenol aromatic ring.

It is thus accordingly proposed to halogenate estrogens in the 1-position to stabilize the compounds while lessening the halo/hydroxyl interaction on the aromatic ring, thereby preserving biological activity of the native estrogen. The present process avoids known synthesis difficulties which have previously precluded preparation of comparable 1-haloestrogens, particularly the fact that, while the 2- and 4-positions of the phenol are highly active, the 1-position is meta to the hydroxy group, and is consequently deactivated; preferential direct electrophilic substitution at the 1-position of the aromatic ring is thus highly improbable.

SUMMARY OF THE INVENTION

The invention comprises a method for the halogenation and reduction of estrones of the formula I, or derivatives thereof:

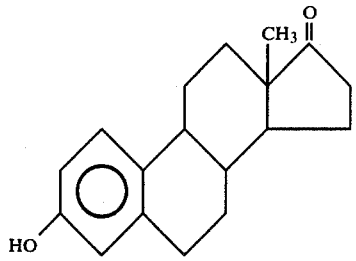

to form corresponding novel 1-haloestradiols of the formula VI;

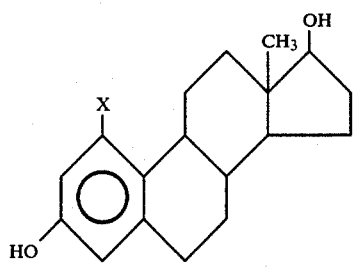

wherein X is a halogen atom, or a radioisotope thereof.

The synthesis can be completed in a short period of time, usually under about two hours, which accomodates the use of radiohalogens, which have characteristically short half lives. Further, the synthesis minimizes extensive work-up procedures between steps, which reduces handling of radioisotopes and consequent exposure to radioactivity.

DETAILED DESCRIPTION OF THE INVENTION

According to the process of the invention, direct electrophilic halogenation of the estrone aromatic ring is preceded by a series of steps which function to: (a) mask the sensitive 3-hydroxy group on the estrone starting material; (b) place an amino substituent at the 4-position of the aromatic ring to direct the subsequent halo reactant to the 1-position; and (c) reduce the cyclopentanone moiety to the corresponding alcohol moiety, according to the following reaction scheme:

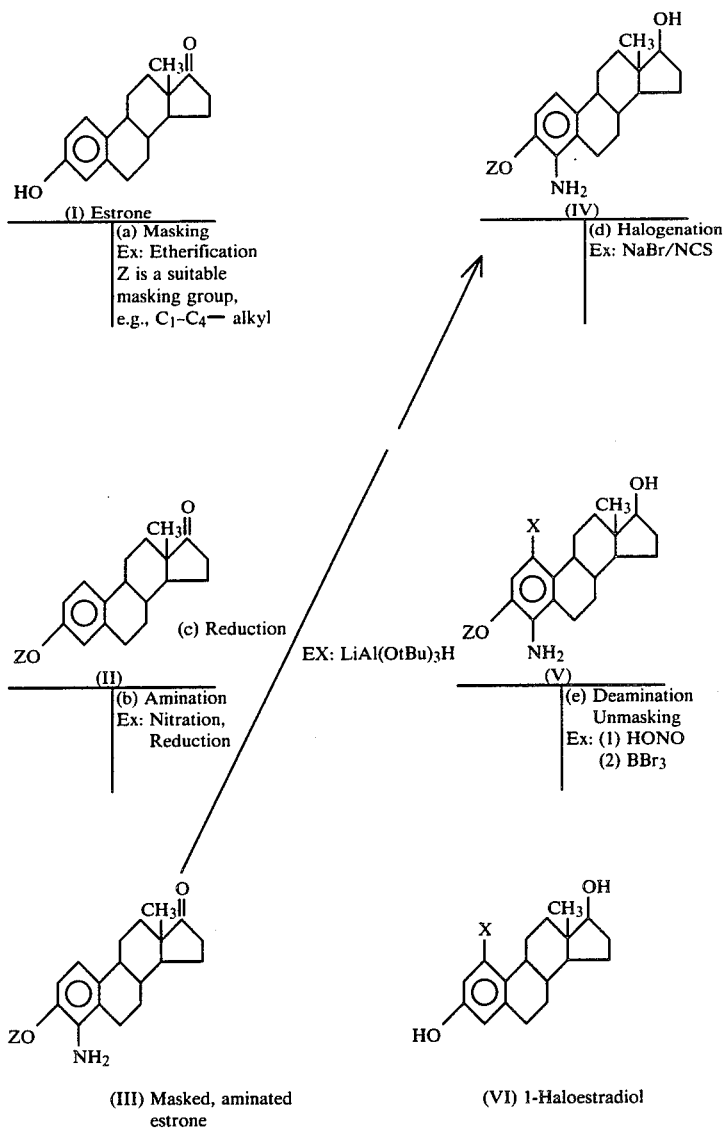

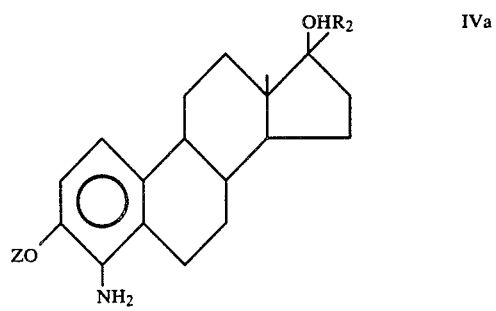

(VI) 1-Haloestradiol

The starting estrone is readily commercially available. In addition to the simple estradiol derivatives of the Formula IV, substituted estradiols comprising derivatives of compounds of the Formula IV are useful, such as compounds of the Formula IVa:

IVa wherein Z is alkyl, especially $C_1$–$C_4$-alkyl, and $R_2$ is alkyl, alkenyl, or alkynyl, especially ethynyl. These compounds, and similar R-substituted 4-amino masked estradiols are prepared in comparable fashion from the starting estrone.

The masking group is adapted to protect the phenolic hydroxyl during the course of the reaction, and must comprise a group which is stable during the subsequent amination, which permits halogenation, and which is removable to provide the desired estradiol at the end of the reaction. Compounds of the Formula II wherein Z is methyl, i.e., 4-aminoestrone-3-methylether, appear to be particularly suitable, whereas tetrahydropyranyl and methoxyethoxy methylethers appear to be unsuitable phenolic protecting groups, as while bromination was successful, deamination could not be completed.

As a practical matter, masking (step a) and amination (step b) are conducted together in known manner, as by nitration, etherification and reduction of the nitro group, as reported by Utne, et al, *J. Org. Chem.* 33:2469–72 (1968), incorporated herein by reference. In this subprocess, the estrone is first nitrated to place nitro groups on the 4-position of the estrone; the masking group, in this instance a methyl ether, is then added by etherification, and the nitro group reduced to give a masked, aminated compound of the Formula III, such as 4-aminoestrone-3-alkylether. This compound is then reduced and halogenated according to the present invention to give an intermediate capable of being unmasked and deaminated to the desired 1-haloestradiol. It is noted that the amination procedure, or a similar procedure which substitutes a group on the 4-position of the aromatic ring (a) which is capable of directing the subsequent halo substituent to the 1-position, and (b) which can readily be subsequently removed, is essential to the process of the invention. In the present exemplified process, nitration of the starting estrone will place nitro groups in the 2- and 4- position on the estrone A-ring; the 4-substituted estrones are separated from the 2-substituted estrones prior to etherification to minimize the presence of 2-nitroestrone and consequently 2-aminoestrone.

The masked, aminated compound of the Formula III is then reduced in step (c) to compounds of the Formula IV, wherein masked 4-aminoestrone is reduced to masked 4-aminoestradiol. The preferred reducing agent is LiAl(OtBu)$_3$H, (lithium aluminum tri-ter-butoxyhydride), as this agent is stereoselective for the desired 17β-alcohol, and thus minimizes contamination with the 17α-alcohol epimer. If some contamination can be tolerated, however, a variety of known reducing agents which will reduce the keto group on the cyclopentanone moiety to the corresponding —OH group, while leaving the rest of the molecule undisturbed, will be useful. Such agents include, for example, LiAlH$_4$ and NaBH$_4$. Useful solvents are known, particularly including tetrahydrofuran (THF).

The masked 4-aminoestradiol of the Formula IV, or suitable derivatives thereof, is then halogenated with an electrophilic halogenating species which will effect electrophilic aromatic substitution in the 1-position thereof. Halogenation with all halogen species, including fluorine, chlorine, bromine, and iodine, and radioisotopes thereof, especially $^{18}$F, $^{123}$I, $^{131}$I, $^{75}$Br, $^{77}$Br and $^{82}$Br are contemplated, with the exception of those species sterically hindered in the 1-position (iodo may be particularly susceptible). Suitable halogenating species include halide salts, especially alkali metal and ammonium salts, in conjunction with species known to promote the electrophilic character of the halogen atom; as is well known in the art, N-chlorosuccinimide (NCS) is a particularly suitable promoter. The use of reaction systems comprising NaX/NCS or NH$_4$X/NCS, in a solvent system such as dioxane-acetic acid which permits a "one-pot" halogenation and deamination reaction, is specifically contemplated.

The resultant masked 1-halo-4-aminoestradiol according to the Formula V is then either isolated as an end product, or treated as an intermediate, without interim isolation. The intermediate is readily deaminated by the process described in U.S. application Ser. No. 619,203 to Hylarides, et al, filed on June 11, 1984 and entitled: DEAMINATION OF AROMATIC AMINES. Deamination and demethylation of the 3-methoxy derivatives of the Formula V are also carried out by known procedures to give 1-haloestradiols of the Formula VI. In an exemplary procedure, deamination of 4-amino-1-bromo-3-methoxyestradiol is accomplished by formation and removal of the corresponding diazonium salt, followed by demethylation of the product (BBr$_3$ in anhydrous methylene chloride). The deamination procedure is broadly applicable to compounds according to the present invention. In general, equimolar quantities of reactants (in all steps a–e) will suffice.

While the description of the invention has particularly been directed to simple derivatives of estrone of the Formula IV, or more complicated estrone derivatives of the Formula IVa, the process of the invention is generally applicable to steroids, particularly estrogen compounds, of the type including a phenolic moiety of the formula:

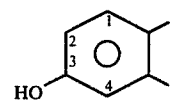

wherein substantially exclusive substitution of halogen in the 1-position is desired, with good yields (50% to 60% of theoretical are contemplated). A further elaboration of the process of the present invention is found in the Hylarides, et al manuscript, "Synthesis of 1-Bromoestradiol", *J. Org. Chem.*: (1984) in press.

The following Examples illustrate the practice of the invention:

EXAMPLE I

A. Preparation of 4-aminoestrone-3-methylether

According to prior art methods (see, e.g., Utne op. cit.)

B. Preparation of 4-aminoestradiol-3-methylether

By reduction of 4-aminoestrone-3-methylether from Example IA, supra

To an ice-cold solution of 4-aminoestrone-3-methylether in 30 ml freshly distilled THF was added 2.64 g (10.4 mmol) of LiAl(OtBu)$_3$H. The resultant reaction mixture was allowed to warm to room temperature and then stirred for an additional 30 minutes. The mixture was then cooled to 0° C. and hydrolyzed by slow addition of water (10 ml), 40% KOH (10 ml), and 1 gm Na tartrate. Ethyl ether (40 ml) was added and the organic phase was washed with water and dried over anhydrous MgSO$_4$. Removal of the solvents under reduced pressure gave 0.74 g (95% of theoretical) yield of 4-amino-3-methoxyestradiol recrystallized from methanol (m.p. 175°–177° C.).

C. Preparation of 1-bromoestradiol-3-methylether

By bromination and deamination of 4-aminoestradiol-3-methylether from Example 1B, supra p A mixture of 89.1 mg. (0.865 mmol) NaBr and 115.1 mg. (0.865 mmol) of NCS in 26 ml of 1:1 dioxane/acetic acid was allowed to stir at 25° C. for 10 minutes. (Solvent systems other than dioxane/acetic acid, such as methanol, may be employed, as known in the art; however, the disclosed system permits a "one pot" bromination and deamination). After the addition of 0.26 g (0.865 mmol) of 4-aminoestradiol-3-methylether (as a solid) the reaction mixture was stirred for an additional one hour to yield 1-bromo-4-aminoestradiol-3-methylether. The pale grey solution was then cooled to 0° C. and 10.59 ml of 0.67M HCl was added, followed by 0.26 ml of 3% $H_2O_2$. Finally, a solution of 60 mg (0.87 mmol) of $NaNO_2$, (comprising a slight excess) in 4.2 ml $H_2O$ was added slowly. The resultant pale yellow solution was allowed to stir at 0° C. for 20 minutes. The reaction mixture was poured into 30 ml 10% KOH and extracted with ethyl acetate. The organic phase was then washed with water, dried over $MgSO_4$, and the solvents removed under reduced pressure to afford 0.21 g of crude product. The crude product was purified by chromatography (MPLC system) using silica gel and 15% ethyl acetate-toluene: 150 mg (50% yield) of 1-bromoestradiol-3-methylether as a white solid was obtained, mp.=118.5° to 120° C.

If required, the 1-bromo-4-aminoestradiol-3-methylether intermediate is stable and can be isolated by the following steps:

The pale gray reaction mixture solution was poured into 60 ml 5% NaOH. The resulting mixture was extracted with Et acetate. The organic phase was washed with 5% NaOH and with $H_2O$. After drying over anhydrous $MgSO_4$, the solvents were removed under reduced pressure. The crude material was purified by MPLC using 15% ethyl acetate-toluene. After isolation, 0.19 g (58% yield) of 1-bromo-4-aminoestradiol-3-methylether as a pale yellow solid was obtained, mp.=55°-60° C.

D. Preparation of 1-bromoestradiol

By demethylation of 1-bromoestradiol-3-methylether from Example IC, supra

A solution of 1-bromoestradiol-3-methylether (116 mg, 0.32 mmoles), and 5 ml $CH_2Cl_2$ was cooled to 0° C. under $N_2$, followed by dropwise addition of 0.64 ml (0.64 mmoles) of 1M $BBr_3$ in $CH_2Cl_2$. The cold bath was removed and the mixture was allowed to stir at 25° C. for 1.25 hours. After the addition of 10 ml of saturated NaCl solution and 20 ml Et-acetate the organic phase was isolated, washed with water and dried over anhydrous $MgSO_4$. Removal of the solvent under reduced pressure gave 100 mg. crude red material, which was chromatographed by MPLC with 15% ethyl acetate-toluene as eluant. Collection of the appropriate fractions followed by removal of solvents gave 50 mg (44% yield) of a white crystalline solid, mp. 239°-241° C. (1-bromoestradiol). The analytical sample was obtained by recrystallization from methanol-water, mp.=242°-244° C.

EXAMPLE II

The procedure of Example I (B-D) is followed except employing 4-amino-17-ethynylestradiol-3-methylether as starting material. The final product is 1-bromo-17α-ethynylestradiol.

EXAMPLE III

Preparation of 1-fluoroestradiol

A solution of 0.1 g (60.334 mmol) of 1-aminoestrone 3-methyl ether in 2.0 ml of acetic acid was cooled to −30° C. at which time 2.2 ml of fluoboric acid was added. After 5 min 26 mg (0.37 mmol) of $NaNO_2$ in 0.2 ml $H_2O$ was added under the surface of the pale-green solution. The resultant red mixture was stirred at −10° C. for 10 min then allowed to warm slowly to 5° C. at which time it was poured into 20 ml cold $H_2O$. The yellow suspension was extracted with $CH_2Cl_2$ (3×25 ml) and the organic phase was subsequently washed with 10 ml saturated NaCl solution, and 10 ml $H_2O$. After drying over anhydrous $MgSO_4$ the solvent was removed under reduced pressure. The crude red product was dissolved in $CH_2Cl_2$ and chromatographed on a florisil column. Removal of the solvent gave 48 mg of a pale yellow solid; 1-fluoroestrone-3-methylether, mp=162°-166° C.

Crude 1-fluoroestrone 3-methylether (46 mg, 0.15 mmol) was dissolved in 8 ml of dry THF under $N_2$. After the addition of 77 mg (0.30 mmol) of LiAl(Ot-Bu)$_3$H the resultant pale-yellow solution was allowed to stir at room temperature for 1.5 hr. The solution was cooled to 0° C. at which time 10 ml of 5% HCl followed by 25 ml of saturated NaCl solution was added. The aqueous phase was extracted twice with 20 ml portions of ethyl acetate. The organic phase was washed with 15 ml of $H_2O$ and dried over anhydrous $MgSO_4$. Removal of the solvents under reduced pressure gave 48 mg of an oil, 1-fluoroestradiol-3-methylether, which later crystallized. TLC (25% ethyl acetate toluene)=0.35.

Crude 1-fluoroestradiol 3-methylether (48 mg, 0.15 mmol) was dissolved in dry $CH_2Cl_2$ and colled to −78° C. under $N_2$. A solution of $BBr_3$ (1M in $CH_2Cl_2$) was added dropwise and a pale-yellow color resulted. After 5 min, the cold bath was removed and the reaction mixture was allowed to stir for an additional 1.5 hr. The pale-red mixture was poured into 50 ml ice-$H_2O$; the resultant suspension was extracted into 10% ethyl acetate chloroform (50 ml). The organic phase was washed with 10 ml $H_2O$, dried over anhydrous $MgSO_4$. Removal of the solvents under reduced pressure gave 1-fluoroestradiol as a pale-red solid. The crude material was dissolved in 10% ethyl acetate/toluene and chromatographed in silica by MPLC. A white solid, 21 mg, was obtained: mp=156°-157° C.

A HNMR and MS was obtained further to characterize the compound. The reaction scheme is set out below.

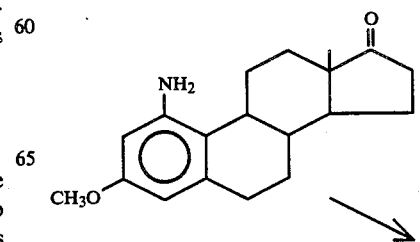

-continued

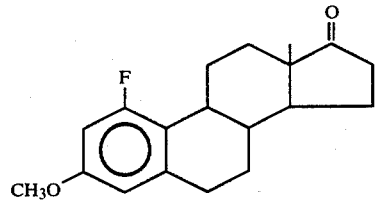

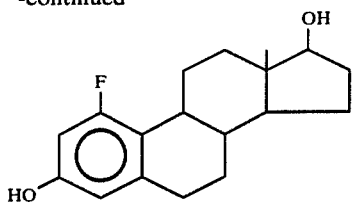

In tests to measure the in vitro binding affinities of each haloestradiol compound to estrogen receptors, 1-fluoroestradiol had the highest affinity, approximately 40% that of the parent estradiol. The affinities of the other compounds were in the range of 8–10% that of estradiol.

What is claimed is:

1. A compound of the formula:

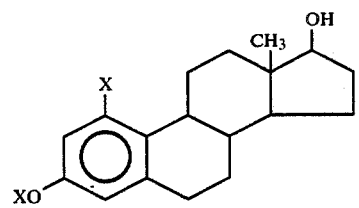

wherein X is fluoro or radio fluoro.
2. The compound of claim 1, wherein X is F.
3. The compound of claim 1, wherein X is $^{18}$F.

* * * * *